United States Patent [19]

Sih

[11] 4,262,131
[45] Apr. 14, 1981

[54] 19-HYDROXY-INTER-PHENYLENE-PG$_1$ COMPONDS

[75] Inventor: John C. Sih, Kalamazoo, Mich.

[73] Assignee: The Upjohn Company, Kalamazoo, Mich.

[21] Appl. No.: 88,444

[22] Filed: Oct. 26, 1979

Related U.S. Application Data

[62] Division of Ser. No. 25,899, Apr. 2, 1979, Pat. No. 4,228,104.

[51] Int. Cl.$^3$ ............................................. C07C 177/00
[52] U.S. Cl. ....................................... 560/53; 562/463
[58] Field of Search ........................... 560/53; 562/463

[56] References Cited

U.S. PATENT DOCUMENTS

| | | | |
|---|---|---|---|
| 3,673,213 | 6/1972 | Zaffaroni | 560/121 |
| 3,903,143 | 9/1975 | Mueller | 560/121 |
| 4,036,876 | 7/1977 | Lanzilotta | 560/121 |
| 4,084,058 | 4/1978 | Nelson | 560/53 |
| 4,100,185 | 7/1978 | Buckler | 560/53 |

*Primary Examiner*—Paul J. Killos
*Attorney, Agent, or Firm*—Robert A. Armitage

[57] ABSTRACT

The present invention provides novel 19-hydroxy-inter-phenylene-PG$_1$ compounds methods for their preparation and pharmacological use for the induction of prostaglandin-like effect.

2 Claims, No Drawings

19-HYDROXY-INTER-PHENYLENE-PG$_1$ COMPONDS

CROSS REFERENCE TO RELATED APPLICATIONS

The present application is a division of Ser. No. 25,899, filed Apr. 2, 1979 now U.S. Pat. No. 4,228,104.

BACKGROUND OF THE INVENTION

The present invention relates to novel prostaglandin analogs. Particularly, these compounds are analogs of the prostaglandins wherein the C-19 position is substituted by hydroxy, i.e., 19-hydroxy-PG compounds. Most particularly, the present invention relates to novel 19-hydroxyinter-phenylene-PG$_1$ compounds, a disclosure of the preparation and use of which is incorporated here by reference from U.S. Pat. No. 4,228,104.

PRIOR ART

Prostaglandin analogs exhibiting hydroxylation in the 19-position are known in the art. See, for example, U.S. Pat. No. 4,127,612, Sih, J. C., Prostaglandins 13:831 (1977) and U.S. Pat. Nos. 3,657,316, 3,878,046, and 3,922,297. See also the additional references cited in U.S. Ser. No. 25,899.

SUMMARY OF THE INVENTION

The present invention particularly provides:
A compound of the formula

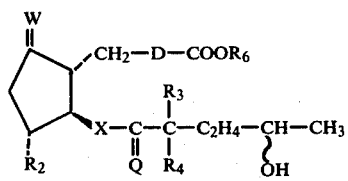

wherein D is
  (1) —(m—ph)—(CH$_2$)$_2$—, or
  (2) —(m—ph)—O—CH$_2$—
wherein —(m—ph)— is inter-meta-phenylene, and
wherein Q is $\alpha$—OH:$\beta$—R$_5$ or $\alpha$R$_5$:$\beta$—OH,
wherein R$_5$ is hydrogen or methyl,
wherein R$_6$ is
  (a) hydrogen,
  (b) alkyl of one to 12 carbon atoms, inclusive,
  (c) cycloalkyl of 3 to 10 carbon atoms, inclusive,
  (d) aralkyl of 7 to 12 carbon atoms, inclusive,
  (e) phenyl,
  (f) phenyl substituted with one, 2,or 3 chloro or alkyl groups of one to 3 carbon atoms, inclusive;

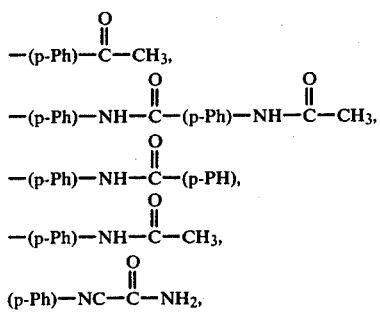

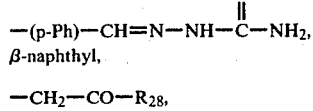

wherein (p-ph) is para-or inter-para-phenylene, phenyl, and R$_{28}$ is phenyl, p-bromophenyl, p-biphenylyl, p-nitrophenyl, p-benzamidophenyl, or 2-naphthyl, or
  (o) a pharmacologically acceptable cation;
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is oxo, methylene, $\alpha$—OH:$\beta$—H, or $\alpha$H:$\beta$—OH; and wherein X is cis- or trans-CH=CH—, or —C≡C—.

With regard to the divalent the substitutents described above (e.g., Q) these divalent radicals are defined as $\alpha$—R$_1$:$\alpha$—R$_J$, wherein R$_I$ represents the substituent of the divalent moiety in the alpha configuration with respect to the ring and R$_J$ represents the substituent of the divalent moiety in the beta configuration with respect to the plane of the ring. Accordingly, when Q is defined as $\alpha$—OH:$\beta$—R$_5$, the hydroxy of the Q moiety is in the alpha configuration, i.e., as in the natural prostaglandin, and the R$_5$ substituent is in the beta configuration.

Specific embodiments of the present invention include:
19(R)-19-hydroxy-3,7-inter-m-phenylene PGF$_{1\alpha}$, p-acetylphenyl ester.

The compounds of the present invention are particularly useful for inducing prostaglandin-like biological effects, as is described in U.S. Ser. No. 25,899. Uses of compounds in accordance with the present invention include, therefore, anti-asthmatic indications.

I claim:

1. A compound of the formula

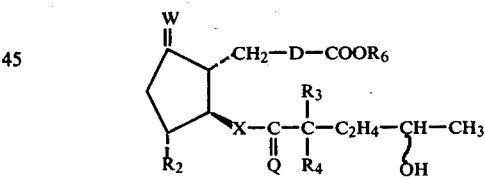

wherein D is
  (1) —(m—ph)—(CH$_2$)$_2$—, or
  (2) —(m—ph)—O—CH$_2$—
wherein —(m—ph)— is inter-meta-phenylene, and
wherein Q is $\alpha$-OH:$\beta$-R$_5$ or $\alpha$-R$_5$:$\beta$-OH,
wherein R$_5$ is hydrogen or methyl,
wherein R$_6$ is
  (a) hydrogen,
  (b) alkyl of one to 12 carbon atoms, inclusive,
  (c) cycloalkyl of 3 to 10 carbon atoms, inclusive,
  (d) aralkyl of 7 of 12 carbon atoms, inclusive,
  (e) phenyl,
  (f) phenyl substituted with one, 2, or 3 chloro or alkyl groups of one to 3 carbon atoms, inclusive;

—(p-Ph)—C(=O)—CH$_3$,  (g)

-continued

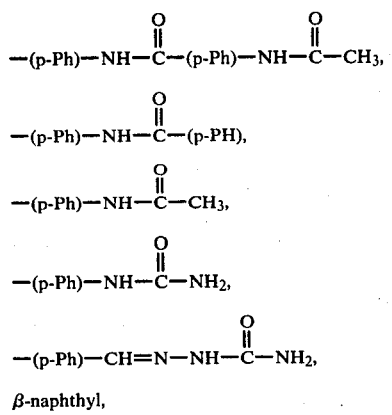

β-naphthyl,

—CH₂—CO—R₂₈, (n)

wherein (p-Ph) is para-phenyl or inter-para-phenylene, and R₂₈ is phenyl, p-bromophenyl, p-biphenylyl, p-nitrophenyl, p-benzamidophenyl, or 2-naphthyl, or (o) a pharmacologically acceptable cation; wherein R₂ is hydrogen, hydroxyl, or hydroxymethyl; wherein R₃ and R₄ are hydrogen, methyl, or fluoro, being the same or different, with the proviso that one of R₃ and R₄ is fluoro only when the other is hydrogen or fluoro;

wherein W is oxo, methylene, α-OH:β-H, or α-H:β-OH; and wherein X is cis- or trans-CH=CH—, or —C≡C—.

2. 19(R)-19-hydroxy-3,7-inter-m-phenylene PGF₁α, p-acetylphenyl ester, a compound according to claim 1.

* * * * *

UNITED STATES PATENT OFFICE
CERTIFICATE OF CORRECTION

Patent No. 4,262,131             Dated 14 April 1981

Inventor(s) John C. Sih

It is certified that error appears in the above-identified patent and that said Letters Patent are hereby corrected as shown below:

In References Cited:
"3,903,143" should read -- 3,903,410 -- and the following references should be included:

```
-- 3,708,492   9/1979    Zaffaroni............560/121
   3,764,673  10/1973    Andersen et al.......560/121
   3,920,827  11/1975    Weinshenker et al....560/121
   4,014,989   3/1977    Zaffaroni............560/121 --
```

Column 1, line 68, "(p-Ph)-NC-$\overset{O}{\overset{\|}{C}}$-NH$_2$," should read -- -(p-Ph)-NH-$\overset{O}{\overset{\|}{C}}$-NH$_2$, --

Column 2, line 8, "wherein (p-ph) is para- or inter-para-phenylene, phenyl," should read -- wherein (p-Ph) is para-phenyl or inter-para-phenylene, --;

Column 4, line 16, "-PGF$_1\alpha$," should read -- -4,5,6-trinor-PGF$_1\alpha$, --.

Signed and Sealed this

Eleventh Day of August 1981

[SEAL]

Attest:

GERALD J. MOSSINGHOFF

Attesting Officer       Commissioner of Patents and Trademarks